United States Patent [19]

Karg et al.

[11] Patent Number: 5,228,456
[45] Date of Patent: Jul. 20, 1993

[54] CONTRACEPTIVE DIAPHRAGM WITH MOLDED PLASTIC RIM

[76] Inventors: Jeffrey A. Karg, 14 Highwood Ave., Waldwich, N.J. 07463; Robert J. Staab, 73 Franklin Turnpike, Allendale, N.J. 07401

[21] Appl. No.: 762,380

[22] Filed: Sep. 19, 1991

[51] Int. Cl.⁵ ............................................. A61F 00/00
[52] U.S. Cl. ..................................... 128/837; 128/830
[58] Field of Search ............... 128/830, 834, 837, 838, 128/839, 840, 841, 842, 843, 846

[56] References Cited

U.S. PATENT DOCUMENTS

| | | | |
|---|---|---|---|
| 1,103,114 | 7/1914 | Warren | 128/834 |
| 1,926,518 | 9/1933 | Findley | 128/834 |
| 2,249,316 | 7/1941 | Lay | 128/834 |
| 2,574,767 | 11/1951 | Stubbs | 128/834 |
| 4,381,771 | 5/1983 | Gabbay | 128/837 X |

FOREIGN PATENT DOCUMENTS

| | | | |
|---|---|---|---|
| 150544 | 3/1953 | Australia | 128/834 |
| 580311 | 7/1959 | Canada | 128/837 |
| 595017 | 3/1960 | Canada | 128/837 |
| 0006609 | 1/1980 | European Pat. Off. | 128/837 |

Primary Examiner—Robert A. Hafer
Assistant Examiner—Sam Rimell
Attorney, Agent, or Firm—Evelyn M. Sommer

[57] ABSTRACT

A contraceptive diaphragm has a cup-shaped body molded from a thermoplastic or thermosetting material, and a rim formed with the diaphragm body having a thickness and an inner core structure sufficient to provide a desired bending resilience for use of the diaphragm without any metal spring therein. The thermoplastic or thermosetting material is preferably a silicone rubber. In one embodiment, the rim is molded with a solid inner core structure with a circular cross-section of between 0.060 to 0.375 inch outer diameter. In another embodiment, the rim is formed by an outer layer molded around an inner core in the form of a plastic, injection- or compression-molded ring. The molded plastic ring is preferably made of an acetal plastic material with an outer diameter of between 0.040 to 0.250 inch. The plastic ring may have two or more cutout portions formed spaced apart along its circumference for defining flexing points on the diaphragm rim.

15 Claims, 2 Drawing Sheets

CONTRACEPTIVE DIAPHRAGM WITH MOLDED PLASTIC RIM

FIELD OF THE INVENTION

This invention generally relates to a contraceptive diaphragm, and more particularly, to one having a molded plastic rim.

BACKGROUND ART

Intravaginal contraceptive devices have become widely accepted as a safe and reliable method of birth control, as well as for the prevention of sexually transmitted diseases. Some devices take the form of a porous, absorbent sponge which is impregnated with spermicidal and/or bacteriocidal agents. Other devices commonly take the form of a diaphragm, made of an elastic film material such as latex, having an annular rim with a resilient metal spring, such as a coiled or leaf spring or flat spring or metal band, incorporated therein.

The metal springs for contraceptive diaphragms are difficult to make, since they must be resilient for bending and durable enough to last with repeated use. For a molded latex diaphragm, the spring is typically a coiled wire that is placed on one mold-half, and latex is poured in the mold so that the spring becomes embedded therein. For a rolled latex diaphragm, a latex sleeve is formed on a mold element by dipping it in the latex, then a spring is placed over the mold base and rolled up in the latex by hand until it is secured therein.

The conventional methods of fabricating contraceptive diaphragms are therefore quite complex, costly, and/or labor-intensive. Furthermore, the metal springs often have coatings of heavy metals, such as cadmium and zinc, for corrosion resistance, which may present a risk of allergic or toxic effects. It is therefore a principal object of the invention to provide a contraceptive diaphragm which does not employ a metal spring and which is simple and inexpensive to make.

SUMMARY OF THE INVENTION

In accordance with the present invention, a contraceptive diaphragm comprises a cup-shaped body molded from a thermoplastic or thermosetting material, and a rim molded integrally with or attached to the diaphragm body made of thermoplastic or thermosetting material having a thickness and an inner core structure sufficient to provide a desired bending resilience for use of the diaphragm without any metal spring therein.

In one preferred embodiment of the invention, the thermoplastic or thermosetting material is a polyurethane or a silicone rubber, the diaphragm body is molded as a film having a film thickness of between 0.005 to 0.050 inch, and the rim is molded with a solid inner core structure with a circular cross-section of between 0.060 to 0.375 inch outer diameter.

In another embodiment of the invention, the rim is molded around an inner core made of a plastic, injection-molded or compression molded ring. The plastic ring is preferably made of Delrin ™ (trademark of DuPont Company) or Valox ™ (trademark of General Electric Co.), acetal plastic or other engineering thermoplastic material, with an outer diameter of between 0.040 to 0.250 inch. The plastic ring may have a plurality of diametrically-opposed cutout portions formed, spaced apart, along its circumference for defining flexing points on the diaphragm rim.

Other objects, features, and advantages of the present invention will become apparent from the following detailed description of the best mode of practising the invention when considered in conjunction with the drawings, as follows:

DESCRIPTION OF THE PREFERRED EMBODIMENTS

Figure 1:
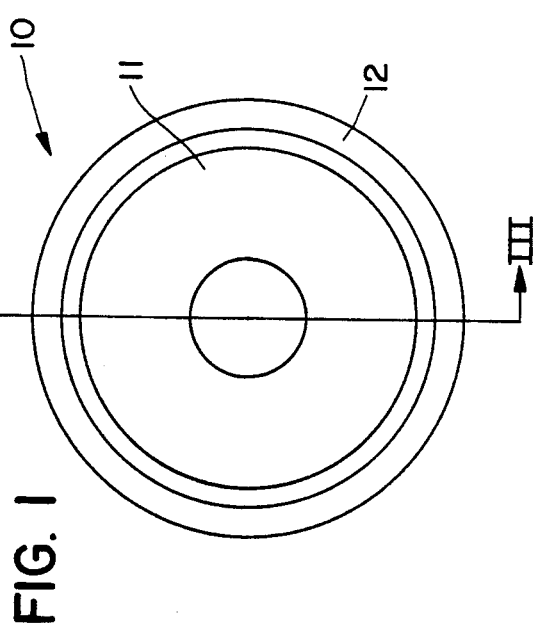
FIG. 1 is a plan view of a contraceptive diaphragm integrally molded of a thermoplastic or thermosetting plastic material in accordance with the invention.
Figure 2:
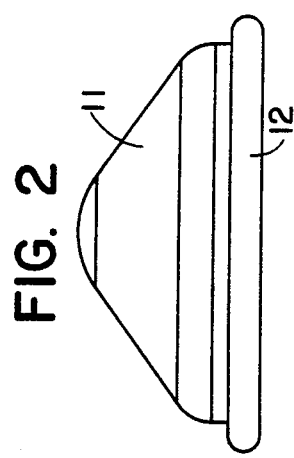
FIG. 2 is a side view of the contraceptive diaphragm in FIG. 1.

Referring to FIGS. 1 and 2, a contraceptive diaphragm 10 in accordance with the present invention is molded from a thermoplastic or thermosetting plastic material to form a cup-shaped body 11. A rim 12 made of thermoplastic or thermosetting material is integrally formed with or attached to the cup-shaped body 11. The material of the rim 12 may be the same as, or different from, that of the cup-shaped body 11. A preferred thermoplastic or thermosetting material is Silastic ™ Q7-4735 silicone rubber made by Dow Corning Company. Silicone rubbers are preferred because they are easily mixed and poured and easily cured to any thickness and without shrinkage. For example, they can be setup in 15 seconds and cured in 5 seconds to 5 minutes. Other materials which can be used include polyurethanes, latex, other elastomers, and rubber, such as Kraton ™ made by Shell Oil Company. The diaphragm body is molded to have a thickness of between 0.005 to 0.050 inch, with a thickness of about 0.015 inch being most preferred.

Figure 3:
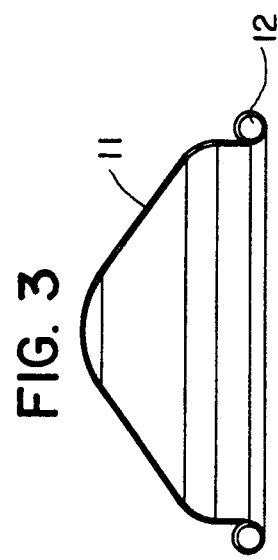
FIG. 3 is a sectional side view, taken along view lines III—III in FIG. 1, showing a solid molded rim in one embodiment of the invention.

The rim 12 is formed with a thickness and an inner core structure sufficient to provide a desired bending resilience for use of the diaphragm without a metal spring. In one embodiment shown in FIG. 3, the rim is molded with a solid inner core structure having a circular cross-section of between 0.060 to 0.375 inch outer diameter. The preferred range is 0.125 to 0.250 inch, with 0.1875 (3/16) inch being most preferred.

Figure 4:
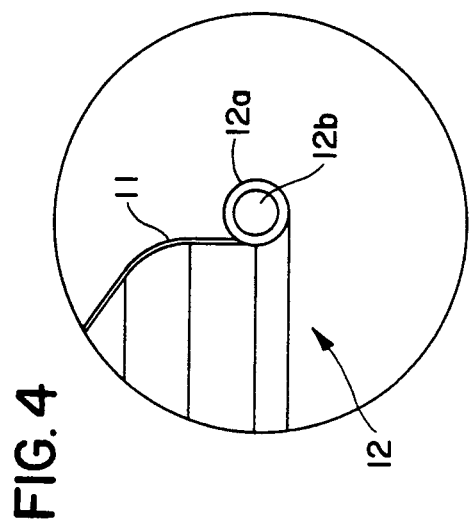
FIG. 4 is a sectional side view of another embodiment having a rim with an inner core made of a molded plastic ring.

In another embodiment shown in FIG. 4, the rim 12 is molded with an outer layer 12a of the same thermoplastic or thermosetting material as the diaphragm body 11, and a separate inner core 12b in the form of a plastic, injection- or compression-molded ring. The molded ring is preferably made from a Delrin ™ (trademark of DuPont Company) or Valox ™ (trademark of General Electric Co.) The plastic ring preferably has an outer diameter or 0.040 to 0.250 inch. The silicone diaphragm body 11 and outer layer 12a is molded around the plastic ring 12b. Instead of a tubular or rod-shaped ring, the inner plastic ring for the diaphragm rim may also be in the form of a flat plastic band.

Figure 7:
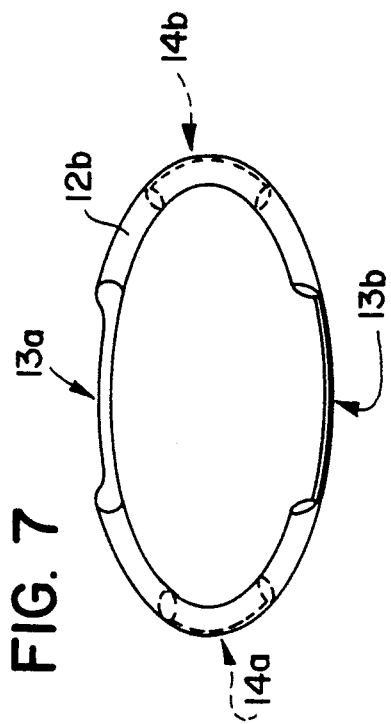
FIG. 7 is a perspective view showing the molded plastic ring having a plurality of cutout portions as flexing points.
Figure 5:
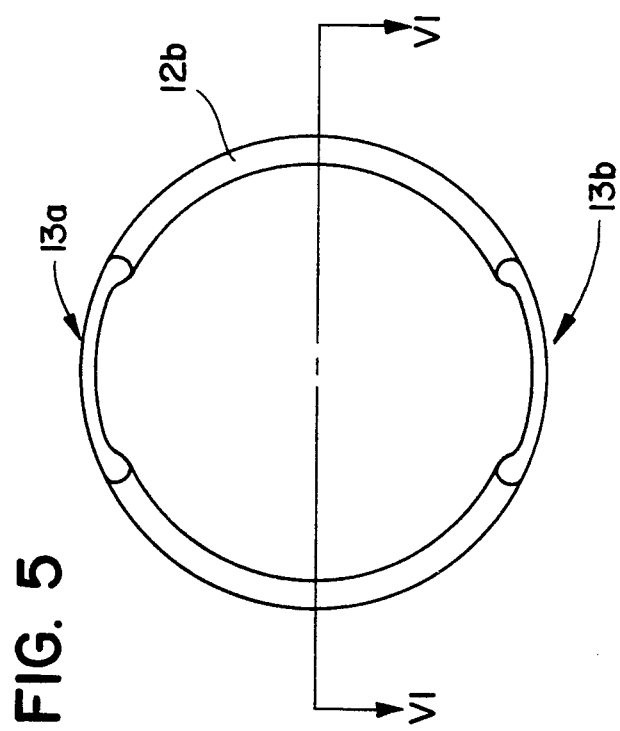
FIG. 5 is a plan view of the molded plastic ring employed in the diaphragm of FIG. 4.
Figure 6:
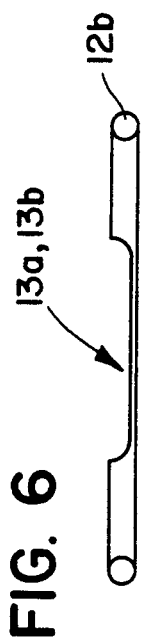
FIG. 6 is a sectional side view of the molded plastic ring employed in the diaphragm of FIG. 4.

In FIGS. 5 and 6, the plastic ring 12b is shown having diametrically-opposed cutout portions 13a, 13b indented along its circumference. The cutout portions define flexing points which can be sensed by hand of the user and which bend more readily than the remainder of the ring. Bending the ring into an elongated shape allows the diaphragm to be inserted easily by hand for use. In FIG. 7, the plastic ring 12b is shown with additional cutout portions 14a, 14b (indicated in phantom line) spaced around the circumference of the ring. The use of a plurality of flexing points allow the ring to be flexed from multiple positions around its circumference.

The present invention thus provides a contraceptive diaphragm using a molded plastic rim or rim with inner plastic ring to eliminate the use of metal springs. The molding process and all plastic construction makes the diaphragm easy to fabricate and greatly reduces its unit costs. The inexpensive, easily fabricated diaphragm can therefore be used as a disposable item, thereby making it safer to use since the risk of infection through reused items is eliminated.

Other modifications may be made given the principles of the invention disclosed above. The embodiments described above and such modifications thereto are intended to be included within the spirit and scope of the invention, as defined in the following claims:

We claim:

1. A contraceptive diaphragm comprising: a cup-shaped body and a rim molded from a thermoplastic or a thermosetting material, having an inner core made of thermoplastic or thermosetting material which is embedded in the rim and which has a selected cross-sectional thickness sufficient to provide a bending resilience for allowing the rim with inner core to be compressed by the user and expanded in position in the vagina so that the diaphragm can be used without any metal spring therein, wherein said inner core has at least one cutout portion formed partway through the cross-sectional thickness of the core and spaced along its circumference for defining at least one corresponding flexing point of the diaphragm rim.

2. A contraceptive diaphragm according to claim 1, wherein said diaphragm body is molded to have a thickness of between 0.005 to 0.050 inch.

3. A contraceptive diaphragm according to claim 1, wherein said rim is molded with a solid inner core structure having a circular cross-section of between 0.060 to 0.375 inch outer diameter.

4. A contraceptive diaphragm according to claim 1, wherein said rim is molded around a separate inner core in the form of a plastic, injection- or compression-molded ring.

5. A contraceptive diaphragm according to claim 5, wherein said molded plastic ring is made from a plastic rod having an outer diameter of between 0.040 to 0.250 inch.

6. A contraceptive diaphragm according to claim 4, wherein said molded plastic ring has a plurality of cutout portions formed spaced apart along its circumference.

7. A contraceptive diaphragm according to claim 1, wherein said cup shaped body and rim are integrally molded from the same thermoplastic or thermosetting material as said inner core.

8. A contraceptive diaphragm according to claim 7, wherein the thermoplastic or thermosetting material is selected from the group consisting of polyurethane and silicone rubber.

9. A contraceptive diaphragm comprising: a cup-shaped body and a rim molded from a thermoplastic or a thermosetting material, having an inner core made of thermoplastic or thermosetting material which is embedded in the rim and which has a selected cross-sectional thickness sufficient to provide a bending resilience for allowing the rim with inner core to be compressed by the user and expanded in position in the vagina so that the diaphragm can be used without any metal spring therein, the inner core being in the form of a plastic, injection- or compression-molded ring, the ring having a pair of diametrically-opposed cutout portions formed partway through the cross-sectional thickness of the ring and spaced along its circumference for defining corresponding flexing points of the diaphragm rim.

10. In a contraceptive diaphragm having a cup-shaped body and a rim formed therewith, the improvement comprising:
an injection- or compression-molded plastic ring which is molded in said rim so as to be embedded therein and to provide an inner core structure having a selected cross-sectional thickness sufficient to provide a bending resilience for allowing the rim with inner core to be compressed by the user and expanded in position in the vagina so that the diaphragm can be used without any metal spring therein, the ring having a pair of diametrically-opposed cutout portions formed partway through the cross-sectional thickness of the ring and spaced among its circumference for defining corresponding flexing points of the diaphragm rim.

11. An improvement in a contraceptive diaphragm according to claim 10, wherein said molded plastic ring has a plurality of cutout portions formed spaced apart along its circumference.

12. An improvement in a contraceptive diaphragm according to claim 10, wherein said molded plastic ring is made from a plastic rod having an outer diameter of between 0.040 to 0.250 inch.

13. A method of making a contraceptive diaphragm having a rim formed therewith, comprising the steps of: making a plastic ring having a selected cross-sectional thickness sufficient for providing a bending resilience for use of the diaphragm without any metal spring therein, and molding the plastic ring into the rim of the diaphragm so as to be embedded therein and to provide a resilient inner core structure for the rim to allow the rim and plastic ring to be compressed by the user and expanded in position in the vagina during use of the diaphragm, the plastic ring having a pair of diametrically-opposed cutout portions formed partway through the cross-sectional thickness of the ring and spaced along its circumference for defining corresponding flexing points of the diaphragm rim.

14. A method of making a contraceptive diaphragm according to claim 13, wherein said plastic ring is made from a plastic rod having an outer diameter of between 0.040 to 0.250 inch.

15. A method of making a contraceptive diaphragm according to claim 13, wherein said plastic ring is provided with a plurality of cutout portions formed partway through the cross-sectional thickness of the ring spaced apart along its circumference.

* * * * *